US011266664B2

(12) United States Patent
DeLuca et al.

(10) Patent No.: US 11,266,664 B2
(45) Date of Patent: *Mar. 8, 2022

(54) USE OF HOMOSALATE AND OCTYL SALICYLATE TO TREAT MULTIPLE SCLEROSIS

(71) Applicant: Wisconsin Alumni Research Foundation, Madison, WI (US)

(72) Inventors: Hector F. DeLuca, Deerfield, WI (US); Steven Marling, Madison, WI (US); Lori A. Plum, Arena, WI (US); Yanping F. Wang, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/549,677

(22) Filed: Aug. 23, 2019

(65) Prior Publication Data

US 2019/0381075 A1 Dec. 19, 2019

Related U.S. Application Data

(63) Continuation of application No. 15/643,988, filed on Jul. 7, 2017, now Pat. No. 10,434,110.

(60) Provisional application No. 62/362,951, filed on Jul. 15, 2016.

(51) Int. Cl.
| | |
|---|---|
| *A61K 31/618* | (2006.01) |
| *A61K 31/60* | (2006.01) |
| *A61K 8/37* | (2006.01) |
| *A61K 9/00* | (2006.01) |
| *A61Q 17/04* | (2006.01) |

(52) U.S. Cl.
CPC .............. *A61K 31/618* (2013.01); *A61K 8/37* (2013.01); *A61K 9/0014* (2013.01); *A61K 9/0019* (2013.01); *A61K 9/0053* (2013.01); *A61K 31/60* (2013.01); *A61Q 17/04* (2013.01); *A61K 2800/91* (2013.01); *A61K 2800/92* (2013.01)

(58) Field of Classification Search
None
See application file for complete search history.

(56) References Cited

U.S. PATENT DOCUMENTS 10,434,110 B2 * 10/2019 DeLuca ............... A61K 9/0014

OTHER PUBLICATIONS

International Search Report and Written Opinion issued in corresponding International Application No. PCT/US2017/041092, dated Aug. 30, 2017, 7 pages.

Agranoff BW & Goldberg D (1974) Diet and the geographical distribution of multiple sclerosis. Lancet (London, England) 2(7888):11061-1066.
Becklund BR, Severson KS, Vang SV, & DeLuca HF (2010) UV radiation suppresses experimental autoimmune encephalomyelitis independent of vitamin D production. Proceedings of the National Academy of Sciences of the United States of America 107(14):16418-6423.
Compston A & Coles A (2002) Multiple sclerosis. Lancet (London, England) 359(9313):1221-1231.
Couteau C, Chauvet C, Paparis E, & Coiffard L (2012) UV filters, ingredients with a recognized anti-inflammatory effect. PloS one 7(12):e46187.
Farah AE & Rosenberg F (1980) Potential therapeutic applications of aspirin and other cyclo-oxygenase inhibitors. British journal of clinical pharmacology 10 Suppl 2:261s-278s.
Goldberg P (1974) Multiple sclerosis: vitamin D and calcium as environmental determinants of prevalence. International Journal of Environmental Studies 6(1):19-27.
Maclaughlin JA, Anderson RR, & Holick MF (1982) Spectral character of sunlight modulates photosynthesis of previtamin D3 and its photoisomers in human skin. Science (New York, N.Y.) 216(4549):1001-1003.
Marusic S, et al. (2008) Blockade of cytosolic phospholipase A2 alpha prevents experimental autoimmune encephalomyelitis and diminishes development of Th1 and Th17 responses. Journal of neuroimmunology 204(1-2):29-37.
Miller H, Newell DJ, & Ridley A (1961) Multiple sclerosis. Trials of maintenance treatment with prednisolone and soluble aspirin. Lancet (London, England) 1(7169):127-129.
Miyamoto K, et al. (2006) Selective COX-2 inhibitor celecoxib prevents experimental autoimmune encephalomyelitis through COX-2-independent pathway. Brain : a journal of neurology 129(Pt 8):1984-1992.
Modi, Khushbu K. et al., "Up-regulation of Ciliary Neurotrophic Factor in Astrocytes by Aspirin: Implications for Remyelination in Multiple Sclerosis," Journal of Biological Chemistry, vol. 288, No. 25, May 7, 2013, p. 18533-18545.
Paulus HE & Whitehouse MW (1973) Nonsteroid anti-inflammatory agents. Annual review of pharmacology 13:107-125.
Rose JW, Hill KE, Watt HE, & Carlson NG (2004) Inflammatory cell expression of cyclooxygenase-2 in the multiple sclerosis lesion. Journal of neuroimmunology 149(1-2):40-49.
Tsau S, Emerson MR, Lynch SG, & LeVine SM (2015) Aspirin and multiple sclerosis. BMC medicine 13:153.
Wang Y, et al. (2013) Suppression of experimental autoimmune encephalomyelitis by 300-315nm ultraviolet light. Archives of biochemistry and biophysics 536(1):81-86.
Wang Y, Marling SJ, Martino VM, Prahl JM, & Deluca HF (2016) The absence of 25-hydroxyvitamin D3-1alpha-hydroxylase potentiates the suppression of EAE in mice by ultraviolet light. The Journal of steroid biochemistry and molecular biology.

* cited by examiner

*Primary Examiner* — Jake M Vu
(74) *Attorney, Agent, or Firm* — Quarles & Brady LLP

(57) ABSTRACT

A method of treating an MS patient with homosalate, octyl salicylate, or a combination is disclosed.

10 Claims, 12 Drawing Sheets

Sunscreen #7 Dose Dependent Test

Sunscreen #5: Time Dependent Test

SS = sunscreen

USE OF HOMOSALATE AND OCTYL SALICYLATE TO TREAT MULTIPLE SCLEROSIS

CROSS-REFERENCE TO RELATED APPLICATIONS

This application is a continuation of U.S. application Ser. No. 15/643,988 filed on Jul. 7, 2017 which claims benefit from U.S. Provisional Application 62/362,951, filed Jul. 15, 2016, the contents of which are incorporated herein by reference for all purposes.

BACKGROUND OF THE INVENTION

Multiple sclerosis (MS), the most common autoimmune disorder affecting the central nervous system, is a demyelinating disease in which the insulating covers of nerve cells in the brain and spinal cord are damaged. The disease affects the ability of parts of the nervous system to communicate and results in physical, mental, and sometimes psychiatric problems. For example, MS patients often have vision disorders, such as blindness in one eye or double vision. Patients also exhibit muscle weakness, trouble with sensation, and trouble with coordination.

The underlying mechanism of MS progression is thought to be either destruction by the immune system or failure of the myelin-producing cells. The cause of the disease is not known, but may include genetics and environmental factors such as viral infections. MS is usually diagnosed based on analysis of a patient's symptoms and the results of supporting medical tests.

Unfortunately, there is no known cure for multiple sclerosis. Current treatments attempt to improve symptoms after an attack and prevent new attacks. Medications used to treat MS are only modestly effective and can have side effects and be poorly tolerated. Physical therapy can help with a patient's ability to function. Because of the lack of good alternatives, many patients pursue unproven alternative treatments. Life expectancy is 5 to 10 years lower than that of an unaffected population.[2]

Needed in the art are new therapeutic compounds for effective MS treatment.

BRIEF DESCRIPTION OF THE DRAWINGS

FIG. 2A: Analysis of different sunscreen ingredients. Avobenzone and oxybenzone partially suppress EAE severity in mice. Mice were treated with sunscreen ingredients (avobenzone, oxybenzone or combination) by topical administration daily during EAE (day 0-day 30). Sunscreen spray was used as a positive control. Each mouse was scored daily and data are expressed as mean values. N=10-12/group. FIG. 2B: Body weights of mice that were administered different sunscreen ingredients. Mice were treated with sunscreen ingredients (avobenzone, oxybenzone or combination) by topical administration daily during EAE (day 0-day 30). Sunscreen spray was also used as a positive control. Each mouse was weighed weekly during the experiment and data are expressed as mean value. N=10-12/group.

FIG. 3A: Sunscreen ingredients (homosalate and octyl salicylate) dramatically suppress EAE development in mice. Mice were treated with sunscreen ingredients (homosalate, octyl salicylate or combination) by topical administration daily during EAE (day 0-day 30). Sunscreen spray was used as a positive control. Mice were scored daily and data are expressed as mean value. N=1-12/group. FIG. 3B: Body weights of mice administered different sunscreen ingredients. Mice were treated with sunscreen ingredients (homosalate, octyl salicylate or combination) by topical administration daily during EAE (day 0-day 30). Sunscreen spray was used as a positive control. Mice were weighed weekly and data are expressed as mean value. N=11-12/group.

FIG. 4A: Topical application of sunscreen prior to NBUVB. Mean score was recorded daily after induction of EAE. FIG. 4B: Body weights were measured weekly. FIG. 4C: Topical application of sunscreen with or without NBUVB completely blocked EAE development. Mean score was measured daily after immunization. Data are expressed as mean±SEM in FIGS. 4A and 4C; Data are expressed as mean±SD in FIG. 4B. All treatment groups in FIGS. 4A, 4B and 4C were statistically different from control group (n=12, p<0.05).

FIG. 5A: Six different sunscreens were topically administered daily and mean score recorded. FIG. 5B: The effect of total darkness on EAE was determined. Treated mice were kept in total darkness for various periods as shown in the legend. Mean score was measured daily. Data are expressed as mean values in FIGS. 5A and 5B. All treatment groups in panel A except BANANA BOAT KIDS and CoTZ FACE were statistically different from control (n=12, P<0.05). No statistical differences were found amongst the groups in panel B (n=12).

FIG. 6A: Disease scores in relation to time of administration of Coppertone Spray sunscreen. Mean score was determined daily. Mice were treated topically with SS 200 µl daily for entire experiment (day 30) with various starting treatment time. Pretreatment: treatment started at day −7 before immunization; Immunization: treatment started at time of immunization; onset: treatment initiated when animals first exhibited a score ≥1.0. FIG. 6B: Body weights determined each week. FIG. 6C: Dose-dependent suppression of EAE by Coppertone Spray sunscreen. FIG. 6D: Body weight was determined weekly. Data are expressed as mean±SEM in FIGS. 6A & 6C; mean±SD in FIGS. 6B & 6D. Pretreatment and Immunization treatments were significantly different from control group in panels A and B (n=12, p<0.05). The two highest levels of SS (50 and 100 µl) were significantly different from control in panels C&D (n=12, p<0.05).

FIGS. 7A and 7B: Mice were treated with a solution of (12% avobenzone, 16% oxybenzone or combination in 25 µl of DMSO) topically each day. Sunscreen (Coppertone spray) (100 µl) was used as a positive control. Each mouse was scored daily (FIG. 7A) and weighed weekly (FIG. 7B) during the experiment. FIGS. 7C and 7D: Mice were treated with two ingredients (30 µl homosalate (1.5 g/kg), 10 µl octisalate (0.5 g/kg) and combination) topically. COPPERTONE SPRAY sunscreen 200 µl was used as a positive control. Mean score (FIG. 7C) and body weight (FIG. 7D) were recorded. Data are expressed as mean value. In FIGS. 7A & 7B, all groups were significantly different from the sunscreen group (n=12, $p<0.05$). In FIGS. 7C and 7D, all treatment groups except octisalate alone were significantly different from the control groups ($p<0.05$).

FIGS. 8A and 8B: Mice were treated with various doses (10, 20 and 30 µl or 0.5, 1.0, 1.5 g/kg) of homosalate or octisalate topically. The mean score (FIG. 8A) and body weights (FIG. 8B) were recorded. FIGS. 8C and 8D, Mice treated with homosalate (30 µl or 1.5 g/kg) topically at various times. Daily mean score (FIG. 8C) and body weight (FIG. 8D) were recorded. Data are expressed as mean value. In FIG. 8A, all treatment groups were significantly different from control ($p<0.05$). In FIG. 8B, all treatments except homosalate 0.5 g/kg were significantly different from control ($p<0.05$); In FIGS. 8C and 8D, the mean scores of homosalate every day and every 2-day were significantly lower than control ($p<0.05$).

DESCRIPTION OF THE PREFERRED EMBODIMENT

Terms

Figure 1:
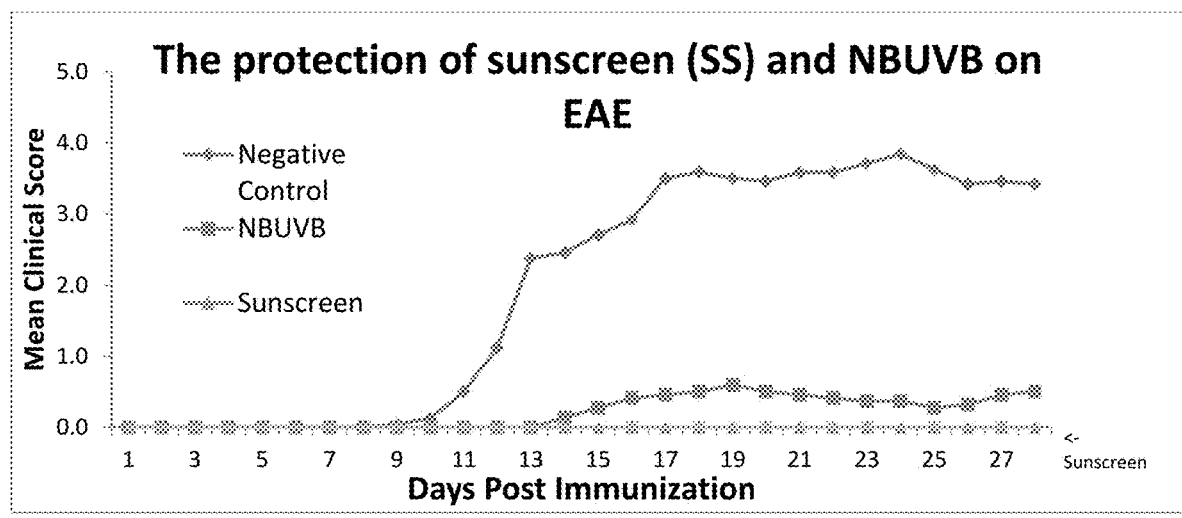
FIG. 1 discloses experiments showing that topical application of sunscreen protects mice from EAE progression. Mice received topical application of sunscreen, NBUVB or both. Each mouse was scored daily after EAE during the entire experiment (day 0-day 28) and data are expressed as mean value. N=10-12/group.

The terms "including" and "comprising" are open-ended terms and should be interpreted to mean "including, but not limited to . . . ." These terms encompass the more restrictive terms "consisting essentially of and "consisting of."

The singular forms "a", "an", and "the" include plural reference. As well, the terms "a" (or "an"), "one or more" and "at least one" can be used interchangeably. The terms "comprising", "including", "characterized by" and "having" can be used interchangeably.

Unless defined otherwise, all technical and scientific terms used herein have the same meanings as commonly understood by one of ordinary skill in the art to which this invention belongs. Each of the publications and patent documents specifically mentioned herein is incorporated by reference in its entirety for all purposes including describing and disclosing the chemicals, instruments, statistical analyses and methodologies which are reported in the publications and which might be used in connection with the invention. All references cited in this specification are to be taken as indicative of the level of skill in the art. Nothing herein is to be construed as an admission that the invention is not entitled to antedate such disclosure by virtue of prior invention.

The "effective amount," as used herein, refers to the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

Unless specifically stated or obvious from context, as used herein, the term "about" is understood as within a range of normal tolerance in the art, for example within 2 standard deviations of the mean. Unless otherwise clear from context, all numerical values provided herein are modified by the term "about."

The term "multiple sclerosis" or "MS," as used herein, refers to an inflammatory disease affecting the nervous system, in which the myelin sheaths around the axons of the brain and spinal cord are damaged, leading to demyelination and scarring as well as a broad spectrum of clinical signs and symptoms. MS may be classified into different disease subtypes, including relapsing/remitting MS (RRMS), secondary progressive MS, primary progressive MS, and progressive relapsing MS. The relapsing-remitting subtype may be characterized by unpredictable relapses followed by periods of months to years of relative quiet (remission) with no new signs of disease activity. The relapsing-remitting subtype may usually begin with a clinically isolated syndrome (CIS). In CIS, a patient may have an attack suggestive of demyelination. Often CIS marks the onset of MS.

A diagnosis of multiple sclerosis can be established on the basis of established clinical symptoms and the clinical symptoms is well known to the skilled person. In one embodiment, the present invention disclose a composition for treating MS by lessening occurrence of the symptom or by slowing or stalling progression of the symptom.

The clinical symptoms of multiple sclerosis may include vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity.

The term "multiple sclerosis" also refers to any other autoimmune disease manifested by demylination of the central nervous system's neurons. The first symptoms which appear at the onset of MS may be referred to at times as "MS-related symptoms." The symptoms of MS in EAE-induced animals (animal model of MS) may be typically weakness and malfunction in the animal's tail, followed by weakness of its rear feet and finally weakness in its front feet. In humans, such first MS-related symptoms may typically be double vision, facial numbness, facial weakness, vertigo, nausea, vomiting ataxia, weakness of the arms, etc.

The term "treating" or "treatment," as used herein, refers to amelioration of some of the undesired symptoms of multiple sclerosis, the prevention of the manifestation of such symptoms before they occur, slowing down or completely preventing the progression of the disease (as may be evident by longer periods between reoccurrence episodes, slowing down or prevention of the deterioration of symptoms etc.), enhancing the onset of the remission period, slowing down the irreversible damage caused in the progressive-chronic stage of the disease (both in the primary and secondary stages), delaying the onset of said progressive stage, or a combination of two or more of the above.

The term "patient" or "subject," as used herein, refers to a mammalian subject (primates (e.g., humans), cows, sheep, goats, pigs, horses, dogs, cats, rabbits, rats, mice and the like), preferably a human subject, that has, is suspected of having, or is or may be susceptible to a condition associated with multiple sclerosis. In one embodiment, the present method may be used for treating a patient who suffers from multiple sclerosis, e.g., with any symptoms as discussed above. In another embodiment, the present method may also be used to prevent a perspective patient from getting multiple sclerosis.

The term "perspective patient," as used herein, refers to any person or subject who may be or is in danger of developing MS.

The term "diagnosing" or "diagnosis," as used herein, refers to detecting a disease or disorder or determining the stage or degree of a disease or disorder such as MS. The term "diagnosis" also encompasses determining the therapeutic effect of a drug therapy to treat MS, or predicting the pattern of response to a drug therapy of MS. The diagnostic methods may be used independently, or in combination with other diagnostic and/or staging methods known in the medical art for a particular disease or disorder, e.g., MS.

The term "pharmaceutically acceptable," as used herein, refers to the compound or composition or carrier being suitable for administration to a subject to achieve the treatments described herein, without unduly deleterious side effects in light of the necessity of the treatment.

The term "therapeutically effective amount" or "pharmaceutically appropriate dosage," as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples may include sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition. Further examples of such carriers include, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration," as used herein, refers to providing the compound or pharmaceutical composition of the invention to a subject suffering from or at risk of the diseases or conditions to be treated or prevented.

The term "systemic delivery," as used herein, refers to any suitable administration methods which may delivery the compounds in the present invention systemically. In one embodiment, systemic delivery may be selected from the group consisting of oral, parenteral, intranasal, inhaler, sublingual, rectal, intracisternal, and transdermal, intravaginal, intraperitoneal, topically (as by powders, ointments or drops), bucal or as an oral or nasal spray administrations. The term "parenterally" as used herein, refers to modes of administration which include intravenous, intramuscular, intraperitoneal, intrasternal, subcutaneous and intraarticular injection and infusion.

In one embodiment, the present compositions or formulations may be administered topically.

The term "topical administration," as used herein, refers to local administration of a component of a composition or a kit of the invention onto the surface of a skin or mucosal tissue of a subject. A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location.

Methods of the Present Invention

The present invention includes methods of using octyl salicylate and/or homosalate, or a composition comprising at least one of octyl salicylate and homosalate, to prevent or suppress the progression of multiple sclerosis. The Examples below show that Applicants observed that commercial sun block preparations decreased or prevented the incidence of EAE in EAE mice, a mouse model of MS. Specifically, Applicants demonstrate that treating a multiple sclerosis (MS) patient or a prospective MS patient with an effective amount of a composition selected from the group consisting of homosalate, octyl salicylate and combinations of homosalate and octyl salicylate can prevent the development of experimental autoimmune encephalomyelitis, thus treating MS. In contrast to the use of sunscreens that comprise octyl salicylate and homosalate, the method of the present invention requires the use of the composition daily for at least 30 days and preferably at least 60 or 90 days. Additionally, a preferable form of administration of the present invention is orally, by inhalation or parenterally, in contrast to topical sunscreen administration.

The method of the present invention includes the step of diagnosing a group of subjects (e.g., humans) in danger of developing MS and identifying an MS patient or a perspective MS patient exhibiting at least one symptom of MS.

Identification of a subject or patient appropriate for treatment of MS symptoms can be carried out based on standardized diagnostic criteria widely used by practicing physicians, especially in the first stages of the disease, such as the so-called Schumacher and Poser criteria (Compston A, Coles A, October 2008, Multiple sclerosis. Lancet 372 (9648): 1502-17; Trojano M, Paoliceili D, (2001) The differential diagnosis of multiple sclerosis: classification and clinical features of relapsing and progressive neurological syndromes. *Neurol, Sci*. 22 (Suppl 2): S98-102; Poser C M, Brinar V V (2004) Diagnostic criteria for multiple sclerosis: an historical review. Clin Neurol Neurosurg 108 (3): 147-58), or the McDonald criteria, which focus on a demonstration with clinical, laboratory and radiologic data of the dissemination of MS lesions in time and space (Compston A, Coles A, October 2008, Multiple sclerosis. Lancet 372 (9648): 1502-17; McDonald W I, Compston A, Edan G et al, (2001) Recommended diagnostic criteria for multiple sclerosis: guidelines from the International Panel on the diagnosis of multiple sclerosis. Ann. Neurol. 50 (1): 121-7; Polman C H, Reingold S C, Edan G et al., (2005) Diagnostic criteria for multiple sclerosis: 2005 revisions to the "McDonald Criteria". *Ann. Neurol,* 58 (6): 840-6).

The most commonly used diagnostic tools for MS are neuroimaging, analysis of cerebrospinal fluid and evoked potentials. In a positive diagnosis, magnetic resonance imaging (MRI) of the brain and spine shows areas of demyelination (lesions or plaques). Gadolinium administered, as a contrast agent, to a patient with MS typically localizes in these "hot spots" or lesions, and can be easily identified with the use of MRI. The MRI of the lesions is one of the most efficient methods of diagnosing MS. Measuring the development of new lesions is also a critical and efficient method of monitoring the progression of MS.

Alternatively, MS can be diagnosed with other known methods. For instance, an MS patient may respond less actively to stimulation of the optic nerve (which may be examined using visual and sensory evoked potentials) and sensory nerves due to demyelination of these nerve pathways (Gronseth G S, Ashman E J, (2000) Practice parameter: the usefulness of evoked potentials in identifying clinically silent lesions in patients with suspected multiple sclerosis (an evidence-based review): Report of the Quality Standards Subcommittee of the American Academy of Neurology. *Neurology* 54 (9): 1720-5). Chronic inflammation of the central nervous system can be demonstrated by an analysis of cerebrospinal fluid. The cerebrospinal fluid is tested for oligoclonai bands, which are present in 75-85% of people with MS (McDonald W I, Compston A, Edan G et al, (2001) Recommended diagnostic criteria for multiple sclerosis: guidelines from the International Panel on the diagnosis of multiple sclerosis. Ann. Neurol. 50 (1): 121-7; Link H, Huang Y M, (2008) Oligoclonai bands in multiple sclerosis cerebrospinal fluid: an update on methodology and clinical usefulness. J. Neuroimmunol. 180 (1-2): 17-28).

In one embodiment, the method of diagnosing an MS patient or a perspective MS patient may include the steps of diagnosing or identifying a subject with one or more of a delay of onset of MS symptoms, with a reduction of peak of severity of MS symptoms, and/or with a decrease of the cumulative disease index (CDI).

One would monitor the patient's MS symptoms and detect a reduction or delay in these symptoms. Most preferably, the development of new lesions in the subject would be monitored on a regular (i.e., semi-annual) basis via MRI. Further symptoms that may be monitored include those selected from the group consisting of changes in sensation (hypoesthesia and paraesthesia), muscle weakness, muscle spasms, or difficulty in moving; difficulties with coordination and balance (ataxia); problems in speech (dysarthria) or swallowing (dysphagia), visual problems (nystagmus, optic neuritis, or diplopia), fatigue, acute or chronic pain, and bladder and bowel difficulties. Cognitive impairment of varying degrees and emotional symptoms of depression or unstable mood are also common. One common clinical measure of disability progression and symptom severity is the Expanded Disability Status Scale or EDSS.

In one embodiment, the patient's symptoms may include vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity, muscle weakness/numbness, and/or paralysis.

In one specific embodiment, the patient's symptom includes paralysis.

In another embodiment, the patient's symptom includes muscle weakness/numbness.

EAE (experimental autoimmune encephalomyelitis, sometimes experimental allergic encephalomyelitis) is an animal model of brain inflammation and demyelinating disease of the central nervous system (CNS) that has been successful in developing useful therapeutic agents. The mouse model is widely studied as an animal model of the human CNS demyelinating diseases, including multiple sclerosis and acute disseminated encephalomyelitis (ADEM).

After comparing the ingredients found in the sun blocks, Applicants identified a few possible differences in the ingredients and then narrowed in on four active ingredients in the effective sun blocks: avobenzone, oxybenzone, homosalate and octyl salicylate. Applicants treated EAE mice with each of these four compounds after induction of the disease and monitored progression of the disease. While avobenzone and oxybenzone slightly suppressed disease progression, homosalate and octyl salicylate almost completely prevented EAE development.

In one embodiment, the present invention is a method of treating an MS patient, comprising the steps of identifying an MS patient or a prospective MS patient and treating the patient with an effective amount of a compound selected from the group consisting of octyl salicylate, homosalate and a mixture of octyl salicylate and homosalate, wherein MS symptoms are decreased or eliminated. As disclosed below, the amount of octyl salicylate, homosalate, or a mixture of octyl salicylate and homosalate is not the same as the amount that would be applied to an individual using sunscreen.

In another embodiment, progression of disease symptoms is slowed or stalled.

In one embodiment, the step of identifying an MS patient or a prospective MS patient may include any methods of identification as discussed above and/or any other methods known to one skilled in the art.

For example, one can identify an MS patient or a prospective MS patient by monitoring one of the symptoms which are typical to an MS patient or a prospective MS patient.

In one embodiment, one can monitor one or more symptoms including vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity, muscle weakness/numbness, and/or paralysis.

In one specific embodiment, the monitored symptom includes paralysis.

In one specific embodiment, the monitored symptom is paralysis.

In another embodiment, the monitored symptom includes muscle weakness/numbness.

In another embodiment, the monitored symptom is muscle weakness/numbness.

In one embodiment, the present application uses a composition or a formulation comprising at least one of octyl salicylate and homosalate, to prevent or suppress the progression of multiple sclerosis in a patient.

In one embodiment, the present application may include at least one of octyl salicylate and homosalate as the sole active compounds for treating, preventing or suppressing the progression of multiple sclerosis in a patient.

In another embodiment, the present application may include at least one of octyl salicylate and homosalate along with other active compounds for treating, preventing or suppressing the progression of multiple sclerosis in a patient.

In one embodiment, the target patient may be a mammalian subject (primates (e.g., humans), cows, sheep, goats, pigs, horses, dogs, cats, rabbits, rats, mice and the like), or a human subject. In one embodiment, the patient is preferably a human being.

In one embodiment, a patient of the human subject is suspected of having, or is or may be susceptible to a condition associated with multiple sclerosis.

In one embodiment, the present application includes the step of identifying an MS patient or a prospective MS patient. For example, an MS patient or a prospective MS patient for the present application may be identified by monitoring one or more symptoms including vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity, muscle weakness/numbness, and/or paralysis of the subject.

In one embodiment, the step of identifying an MS patient or a prospective MS patient is by monitoring the symptom of paralysis or muscle weakness/numbness.

In one embodiment, the step of identifying an MS patient or a prospective MS patient is by monitoring the symptom of paralysis.

In one embodiment, the step of identifying an MS patient or a prospective MS patient is by monitoring the symptom of muscle weakness/numbness.

In one embodiment, one can continue monitoring the symptom of the patient during the treatment process for the purpose of evaluation of the treatment. For example, a patient's symptom such as paralysis or muscle weakness/numbness may be monitored during the treatment so that the patient's treatment can be evaluated. As an example, the success of the treatment can be shown when occurrence of MS symptom is lessened or progression of the symptom is slowed or stalled after the treatment.

After an MS patient or a prospective MS patient is identified, the MS patient or the prospective MS patient is treated with a therapeutically effective amount of a composition or formulation comprising a substance selected from the group consisting of homosalate, octyl salicylate and combinations of homosalate and octyl salicylate.

In one embodiment, the substance selected from the group consisting of homosalate, octyl salicylate and combinations of homosalate and octyl salicylate is the only active substance used in the present application. Thus, the MS patient or the prospective MS patient is treated with a therapeutically effective amount of a substance selected from the group consisting of homosalate, octyl salicylate and combinations of homosalate and octyl salicylate.

In another embodiment, the substance selected from the group consisting of homosalate, octyl salicylate and combinations of homosalate and octyl salicylate may be used as one of the active substances. Thus, the MS patient or the prospective MS patient is treated with a therapeutically effective amount of a composition or formulation comprising a substance selected from the group consisting of homosalate, octyl salicylate and combinations of homosalate and octyl salicylate.

The composition or formulation may additionally include any pharmaceutically acceptable carrier, pharmaceutically acceptable sterile aqueous or nonaqueous solutions, dispersions, suspensions or emulsions, adjuvants such as preservatives, wetting agents, emulsifying agents and dispersing agents, or other necessary substances.

In one embodiment, the composition or formulation is either in solid dosage forms or liquid dosage forms.

Liquid dosage forms may include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Solid dosage forms may include capsules, tablets, pills, powders, and granules. In certain embodiments, solid dosage forms may contain from 1% to 95% (w/w) of a compound of the invention. In certain embodiments, the present compounds or pharmaceutically acceptable salts thereof, may be present in the solid dosage form in a range of from 5% to 70% (w/w). In such solid dosage forms, the active compound may be mixed with at least one inert, pharmaceutically acceptable carrier, such as sodium citrate or dicalcium phosphate and/or a), fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Dosage forms for topical administration of the compounds and the formulation described herein include powders, sprays, ointments, and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

A compound of the invention may also be administered in sustained release forms or from sustained release drug delivery systems.

In one embodiment, the compounds, compositions and the formulations may be administered by a method of oral, parenteral, intranasal, inhaler, sublingual, rectal, intracisternal, and transdermal, intravaginal, intraperitoneal, topically (as by powders, ointments or drops), bucal or as an oral or nasal spray administrations.

In one embodiment, the compounds, compositions and the formulations may be administered by oral, parenteral or topical method.

In one embodiment, the compounds, compositions and the formulations may be administered topically.

In some embodiments, the dose of the invention regarding homosalate and/or octisalate is at least about 0.1 g/kg per body weight. In other embodiments, the dose of the invention regarding homosalate and/or octisalate is at least about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 g/kg per body weight. In further embodiments, the dose of the invention regarding homosalate and/or octisalate is between about 0.5 to about 15 g/kg per body weight. In other embodiments, the dose of the invention regarding homosalate and/or octisalate is between about 0.5-14, 1-10, 2-10, 1-8, 1-5 or 0.5-2 g/kg per body weight.

In one embodiment, homosalate and/or octisalate is administered as the only active ingredient in a composition or formulation as discussed above. For example, a composition of homosalate and/or octisalate may be administered to a MS patient or a perspective patient. The composition of homosalate and/or octisalate may be combined with other components such as any pharmaceutically acceptable carrier, pharmaceutically acceptable sterile aqueous or non-aqueous solutions, dispersions, suspensions or emulsions, adjuvants such as preservatives, wetting agents, emulsifying agents and dispersing agents, or other necessary substances.

In one embodiment, Applicants envision homosalate and/or octisalate may be administered as one of the multiple active ingredients for treating MS. For example, Applicants envision that homosalate and/or octisalate may be used with other MS treatment protocols such as cyclooxygenase (COX) inhibitors and others In one embodiment, the method of using the compounds, compositions and the formulations as discussed above for treating MS is dose-dependent. For example, to achieve a better treatment of MS, 0.8, 0.85, 0.9, 0.95, 1.0, 1.05, 1.1, 1.15, 1.2, 1.25, 1.3, 1.35, 1.4, 1.45, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 g/kg per body weight of homosalate and/or octisalate may be administered to a MS patient or a perspective MS patient.

Preferably, 1.0, 1.05, 1.1, 1.15, 1.2, 1.25, 1.3, 1.35, 1.4, 1.45, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 g/kg per body weight of homosalate and/or octisalate may be administered to a MS patient or a perspective MS patient.

Figure 8A:
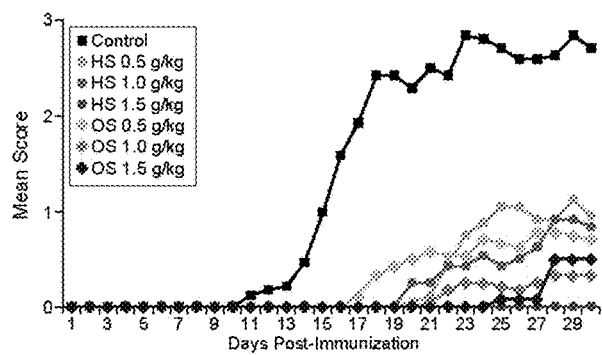
FIGS. 8A, 8B, 8C and 8D show dose dependent suppression of EAE by homosalate (HS) and octisalate (OS).
Figure 8B:
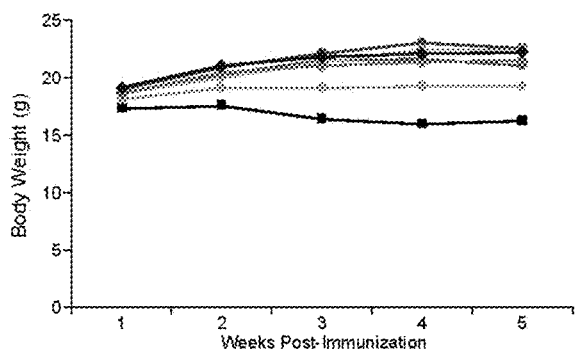
Figure 8C:
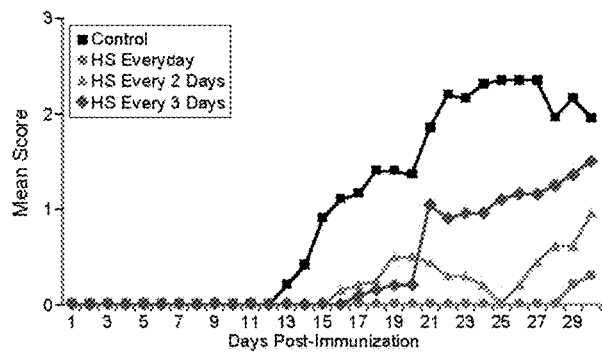
Figure 8D:
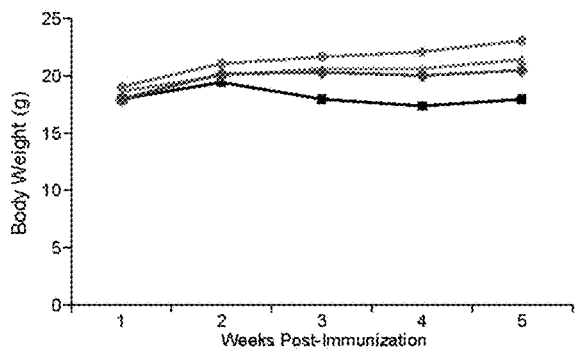
Figure 9A:
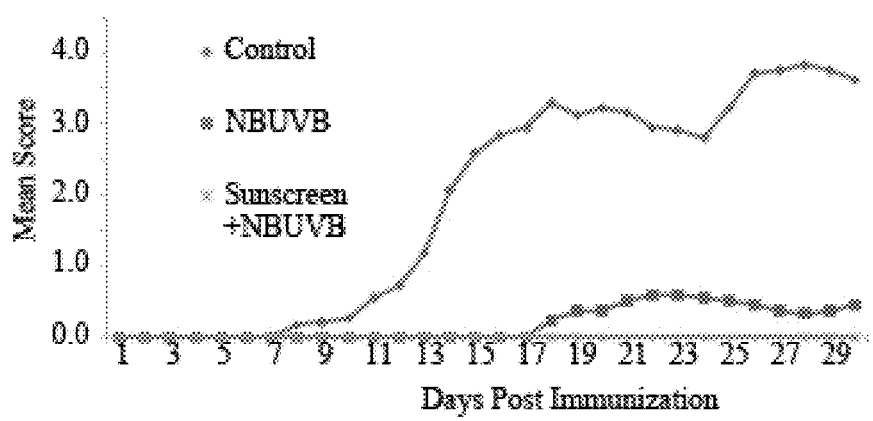
FIGS. 9A, 9B, and 9C show that all of the tested sunscreens protect the mice from developing EAE.
Figure 9B:
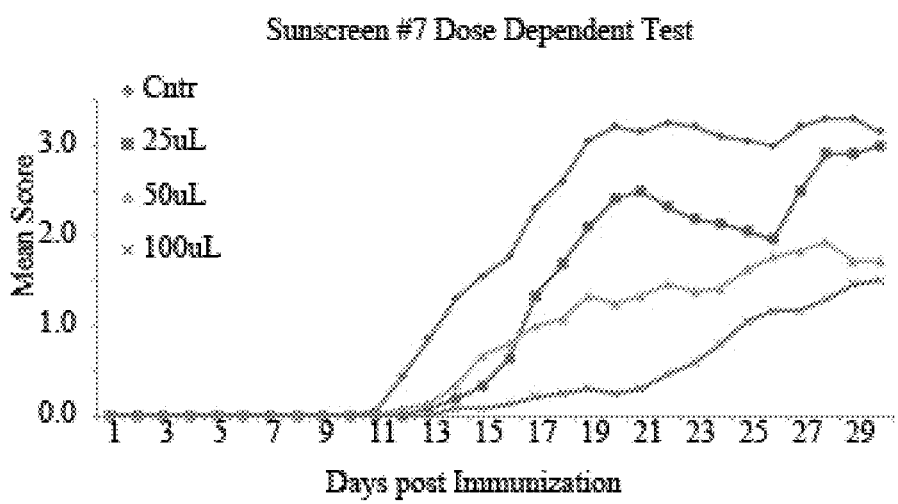
Figure 9C:
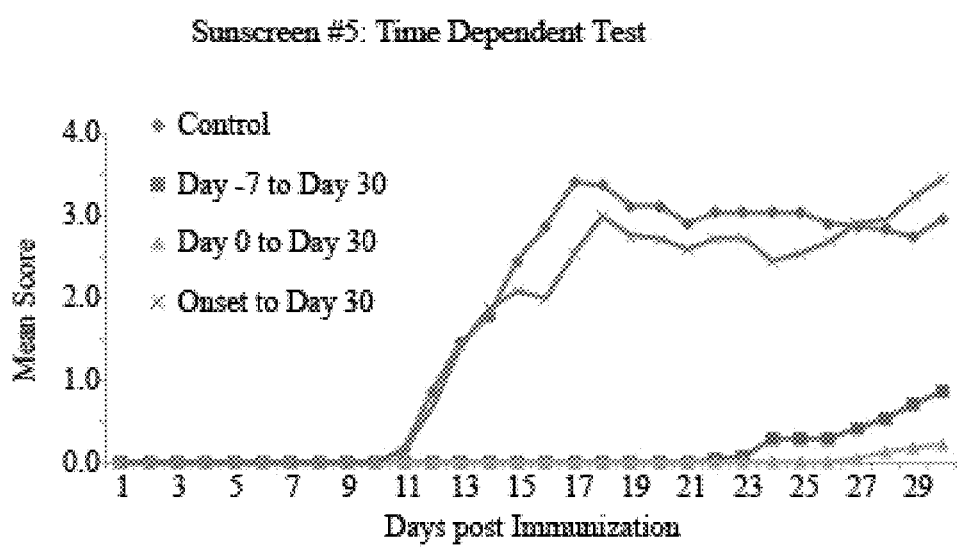
Figure 10A:
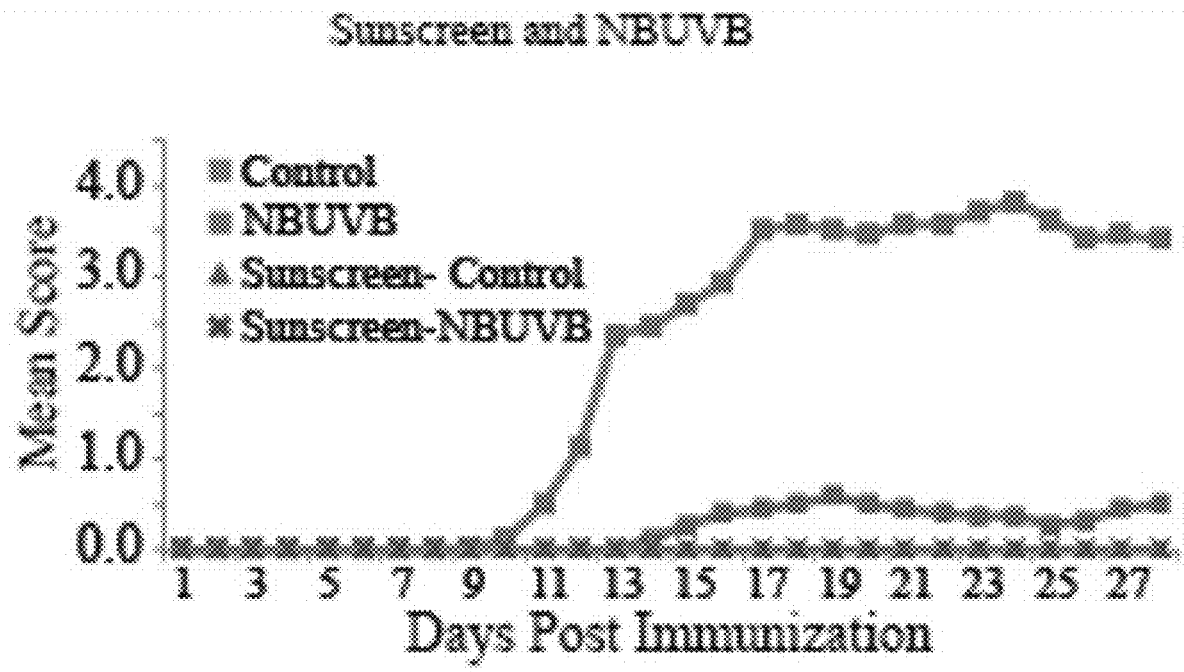
FIGS. 10A, 10B, 10C, 10D, 10E and 10F show that all of the tested sunscreens protect the mice from developing EAE.
Figure 10B:
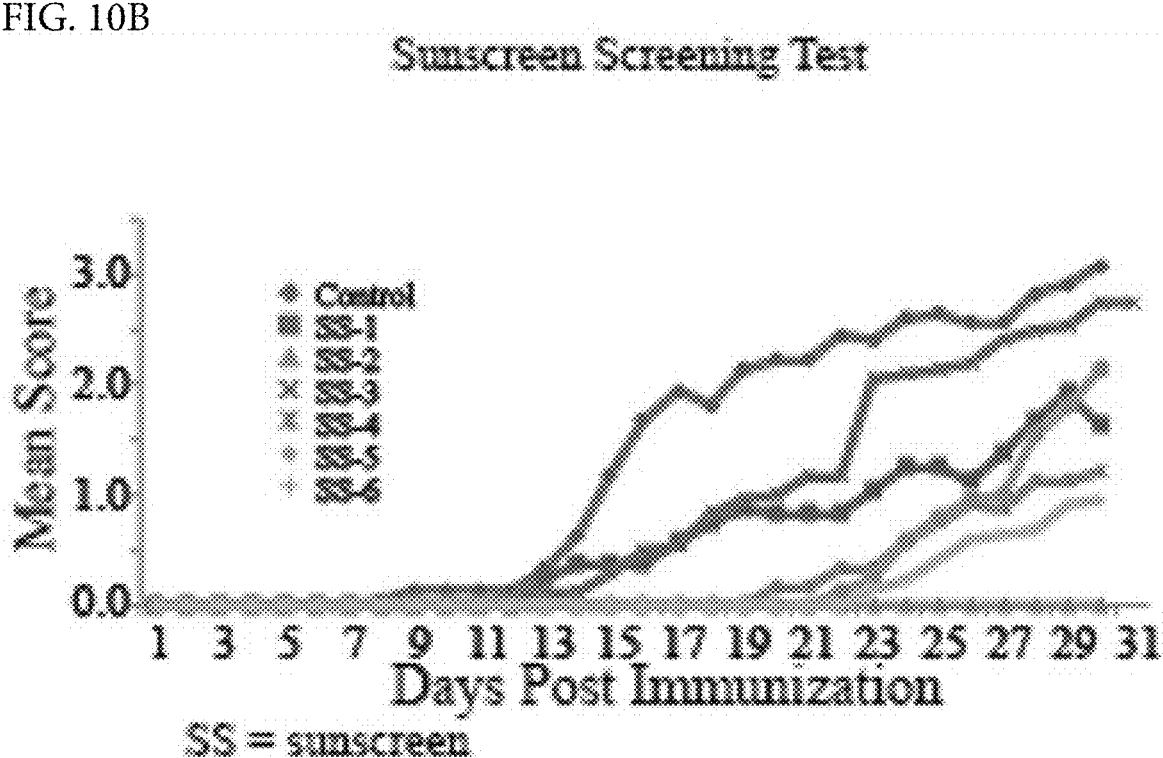
Figures 10C, 10D:
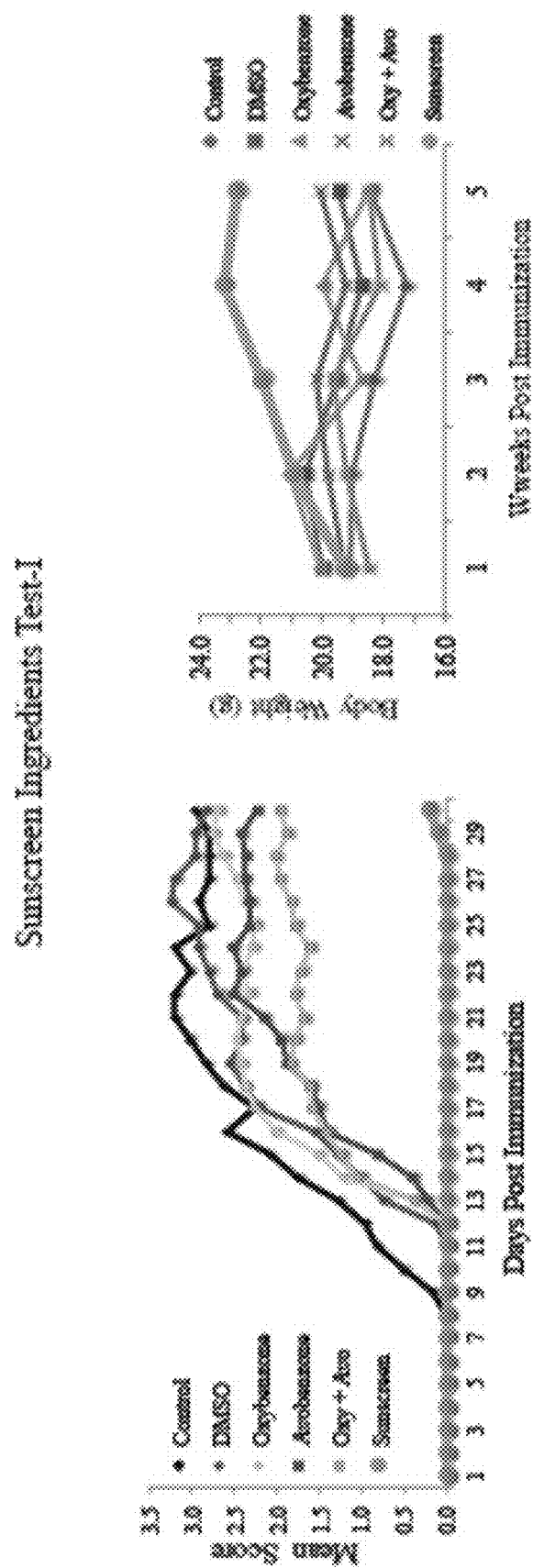
Figures 10E, 10F:
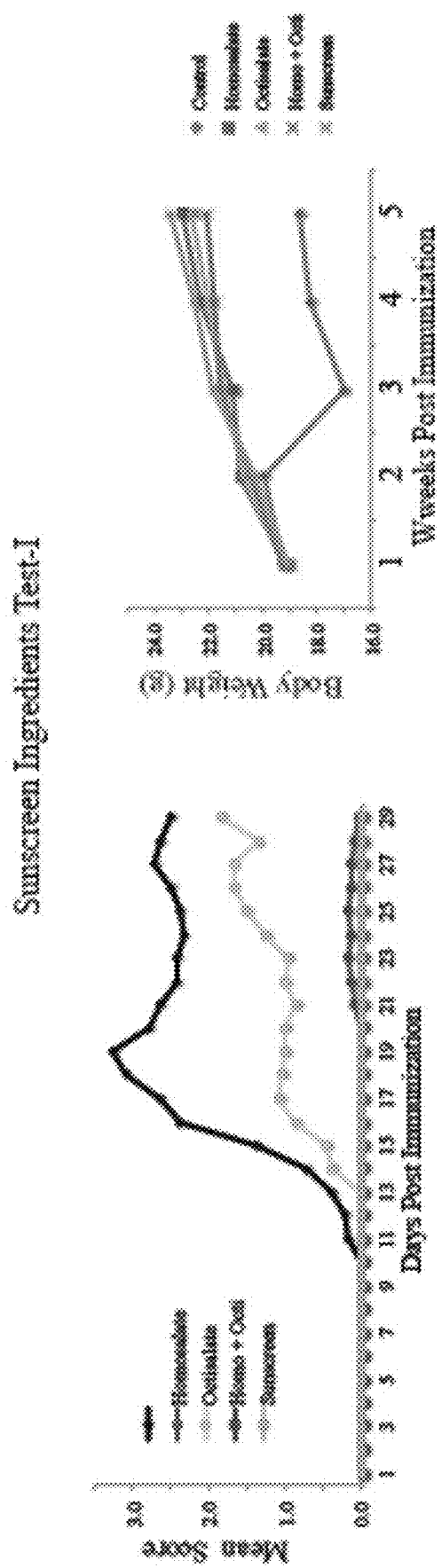

FIGS. 8A, 8B, 8C and 8D show dose dependent suppression of EAE by homosalate (HS) and octisalate (OS). FIGS. 8A and 8B: Mice were treated with various doses (10, 20 and 30 μl or 0.5, 1.0, 1.5 g/kg) of homosalate or octisalate topically. The mean score (FIG. 8A) and body weights (FIG. 8B) were recorded. FIGS. 8C and 8D, Mice treated with homosalate (30 μl or 1.5 g/kg) topically at various times. Daily mean score (FIG. 8C) and body weight (FIG. 8D) were recorded. Data are expressed as mean value. In FIG. 8A, all treatment groups were significantly different from control (p<0.05). In FIG. 8B, all treatments except homosalate 0.5 g/kg were significantly different from control (p<0.05); In FIGS. 8C and 8D, the mean scores of homosalate every day and every 2-day were significantly lower than control (p<0.05).

Preferred Patients

A preferred patient of the present invention is an MS patient who exhibits at least one of the following autonomic, visual, motor, or sensory symptom: loss of sensitivity or changes in sensation such as tingling, numbness, muscle weakness, very pronounced reflexes, muscle spasms, or difficulty in moving; difficulties with coordination and balance (ataxia); problems with speech or swallowing, visual problems (nystagmus, optic neuritis or double vision), feeling tired, acute or chronic pain, bladder and bowel difficulties, confused thinking, emotional problems such as depression or unstable mood, Uhthoff's phenomenon (a worsening of symptoms due to exposure to higher than usual temperatures) or Lhermitte's sign (an electrical sensation that runs down the back when bending the neck).

One may also wish to measure therapeutic outcome by using conventional MS monitoring rubrics. For example, disability and severity can be measured by the expanded disability status scale (EDSS) or the multiple sclerosis functional composite. Magnetic resonance may also be used to show a reduction in new lesions in the nervous system.

The definition of "symptom" includes all these parameters.

Another preferred patient of the present invention is a patient in danger of developing MS or a "prospective patient."

Preferred patients may be pediatric patients, geriatric patients or adult patients. Preferred patients may be either male or female.

Preferred Therapeutic Compositions

The method of the present invention requires exposing a patient to octyl salicylate, homosalate or a combination of both.

Octyl salicylate; 2-ethylhexyl salicylate; 2-ethylhexyl 2-hydroxybenzoate; ethyl hexyl salicylate; 2-ethylhexyl ester salicylic acid; salicylic acid, 2-ethylhexyl ester; benzoic acid, 2-hydroxy-, 2-ethylhexyl ester; 2-ethylhexyl ester benzoic acid, 2-hydroxy-; 2-hydroxy-2-ethylhexyl ester benzoic acid; or octisalate, is an ester formed by the condensation of a salicylic acid with 2-ethylhexanoloften and is used as an ingredient in sun screens and cosmetics to absorb UVB (ultraviolet) rays from the sun. It is typically found as a colorless oily liquid with a slight floral odor. Octyl salicylate can be obtained from Spectrum Chemical MFG. Corp. (New Brunswick, N.J.).

The salicylate portion of the molecule absorbs ultraviolet light, protecting skin from the harmful effects of exposure to sunlight. The ethylhexanol portion is a fatty alcohol, adding emollient and oil-like (water resistant) properties.

The formula for octyl salicylate is presented below:

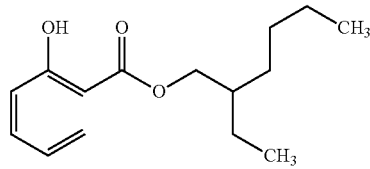 [SMILES: C=C/C=C\C(O)=C\C(=O)OCC(CC)CCCC]

Homosalate, or 3,3,5-trimethylcyclohexyl 2-hydrobenzoate, is an ester formed from salicylic acid and 3,3,5-trimethylcyclohexanol, a derivative of cyclohexanol. The compound is contained in 45% of U.S. sunscreens and is sometimes used as a chemical UV filter. The salicylic acid portion of the molecule absorbs ultraviolet rays with a wavelength from 295 nm to 315 nm, protecting the skin from sun damage. The hydrophobic cyclohexanol portion provides greasiness that prevents it from dissolving in water.

Homosalate can be obtained from Spectrum Chemical MFG. Corp. (New Brunswick, N.J.).

The formula for homosalate is presented below:

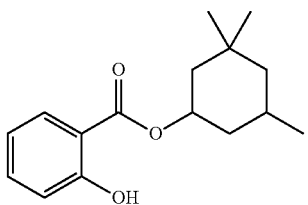 [SMILES: CC1CC(OC(=O)c2ccccc2O)CC(C)(C)C1]

Preferred Methods of Administration

The compounds may be introduced to a patient in a variety of administrative modes. Preferable administration may be topical, intravenous, oral, parenteral, or via inhalation. Other modes of administration will also be within the scope of the present invention.

The Examples below disclose an effective topical dose in a mouse model of 1.5 g/kg each day for homosalate and 0.5 g/kg daily for octyl salicylate. The corresponding human dose would be in the range of 0.1 to 5 g/kg body weight. We predict an effective dose range of 0.1 to 2 g/kg body weight for homosalate and 0.1 to 1 g/kg body weight for octyl salicylate.

An oral, inhalation or parenteral dose will typically be similar to a topical dose.

A preferred dose will achieve an effective systemic concentration of the compound.

Example 1

Materials and Methods

Animals and Diet. Female C57BL/6 mice (8-9 weeks old) purchased from Jackson Laboratory were fed a standard lab diet chow 5008 (Purina Mills, Richmond, Ind.) and maintained in the Department of Biochemistry's vivarium. The mice were exposed to 12 h light-dark cycles. All procedures were approved by the Research Animal Resources Committee of the College of Agricultural & Life Sciences, University of Wisconsin-Madison. The mice were randomly divided into groups for different treatment (12 mice/group).

Sunscreen and Active Ingredients Treatment

Mice were shaved on their back to receive sunscreen or NBUVB radiation. The following Sunscreen cream or spray was used in our study (See Appendix A): 1. Coppertone spray (SPF 50, MSD Consumer Care, Inc., Memphis, Tenn.); 2. Coppertone water babies (SPF 50, MSD Consumer Care, Inc., Memphis, Tenn.); 3. Hawaiian Tropic (SPF 50, Energizer Personal Care, LLC, Shelton, Conn.); 4. Kiss my face (SPF 50, Kiss My Face, LLC, Gardiner, N.Y.); 5. Blue Lizard Australian Sunscreen (SPF 30, Crown Laboratories, Johnson, Tenn.); 6. Banana Boat Kids (SPF 50, Energizer Personal Care, LLC, Shelton, Conn.); 7. CoTZ Face (SPF40, CoTZ Skincare, West Norriton, Pa.). The sunscreen was applied manually to cover the shaved skin daily depending on the experimental schedule. Four main active ingredients (avobenzone; oxibenzone; homosalate; octyl salicylate) were purchased from Spectrum Chemical MFG. Corp. (New Brunswick, N.J.). The total dose of each ingredient administrated topically on each mouse skin was equal to the amount of the ingredient in the sunscreen.

Narrow Band UVB (NBUVB) Treatment

For NBUVB treatment, a set of four TL20W/01 UVB 311 narrow band 2 Ft bulbs (wavelength centered at 311 nm-313 nm, Amjo Corp, West Chester, Ohio) were used. The radiation output was measured by using a UV radiometer equipped with a 302-nm sensor (UVP LLC, Upland, Calif.). Mice were put into a 16-chamber Plexiglas cage individually to receive daily UV radiation from day 7 prior to immunization to day 30 after immunization. Each mouse was rotated in the different chamber to avoid uneven UV radiation in the experiment.

EAE Induction

In this experiment, mice were immunized with myelin oligodendrocyte glycoprotein peptide $(MOG)_{35-55}$. $MOG_{35-55}$ kit (EK-2110) was purchased from Hooke lab (Lawrence, Mass.). Each mouse was immunized with subcutaneous injection of 20 µl $MOG_{35-55}$/CFA emulsion and intraperitoneally injection with 200 ng of pertussis toxin (List Biological Laboratories) diluted in sterile PBS. The second booster pertussis toxin injection was given 48 hours later. Each mouse was scored daily for clinical signs of EAE using the following scale: 0, no clinical disease; 1, loss of tail tone; 2, unsteady gait; 3, hind limb paralysis; 4, forelimb paralysis; 5, death.

Statistical Analysis

Onset was calculated by averaging the first day when clinical signs appeared and continued for at least 2 days. Mean severity was determined by averaging the clinical scores during the entire experiment. The CDI (clinical disease index) was calculated by summing the clinical scores in each animal and divided by the number of mice per group. Statistical analyses were performed using the two-tailed Fisher exact probability test for incidence, the Mann-Whitney nonparametric u test for clinical scores, and the unpaired Student t test for all other measurements. A value of $P<0.05$ was considered statistically significant.

Results

FIGS. 9A, 9B, 9C, 10A, 10B, 10C, 10D, 10E and 10F show the protective effect of various sun screens on mice from developing EAE, although the sunscreens protect at different levels. Testing individual sunscreen ingredients demonstrate that homosalate and octyl salicylate components provide the protection.

Referring to FIG. 1, our data demonstrate that topical application of sunscreen protects mice from EAE progression. Mice received topical application of sunscreen, NBUVB or both after immunization with MOG35-55/CFA emulsion. Each mouse was scored daily after EAE during the entire experiment. Data are expressed as mean value, N=10-12/group.

Figure 2A:
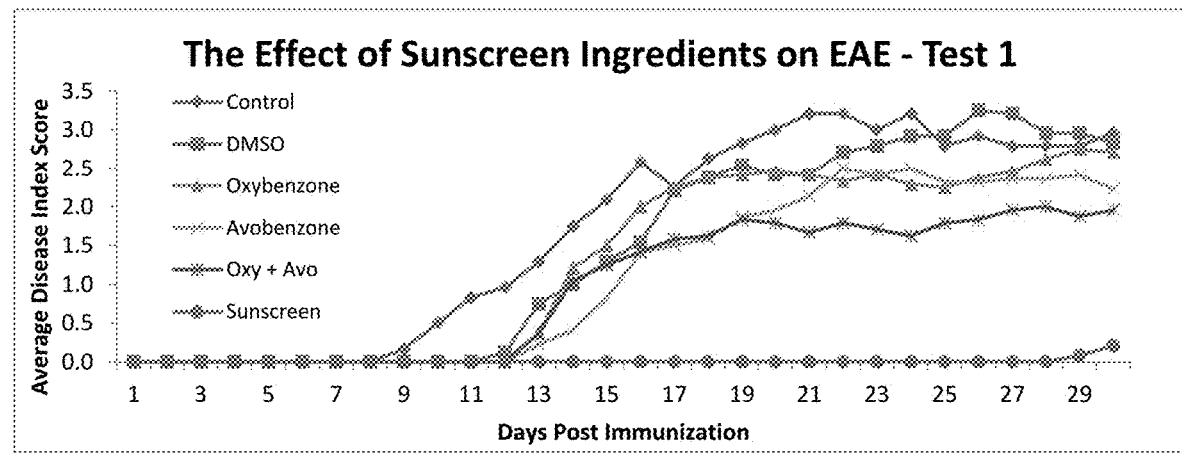
FIGS. 2A and 2B are a set of graphs showing the effect of specific sunscreen ingredients on EAE. Ingredients (avobenzone and oxybenzone) of sunscreen partially suppress EAE severity in mice.
Figure 2B:
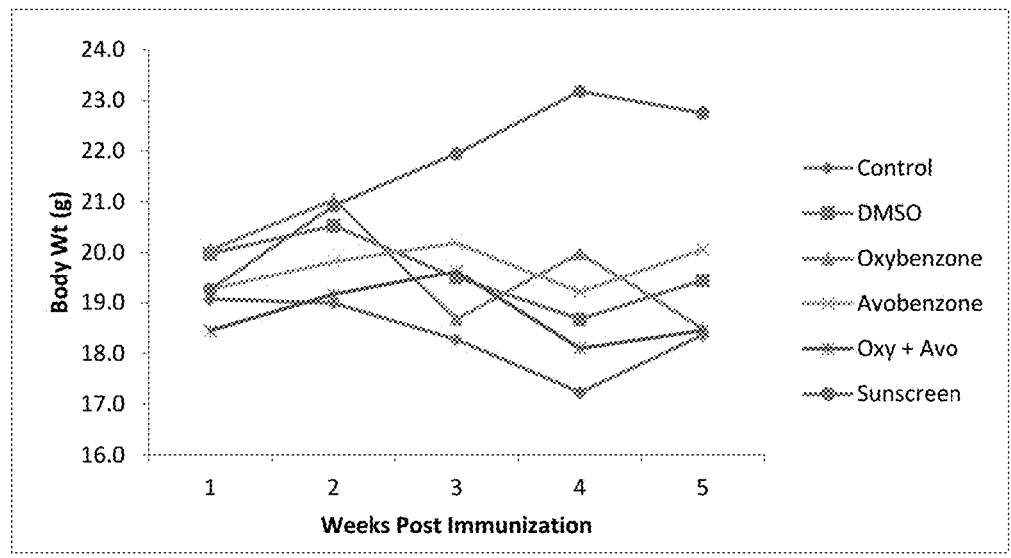

Referring to FIGS. 2A and 2B, we analyzed different sunscreen ingredients. Avobenzone and oxybenzone partially suppress EAE severity in mice. Mice were treated with ingredients (avobenzone, oxybenzone or combination) of sunscreen by topical administration daily during EAE (day 0-day 30). Sunscreen spray 200 µl was also used as a positive control. Each mouse was scored daily and weighed weekly during the experiment (30 days). Data are expressed as mean value, N=10-12/group.

Figure 3A:
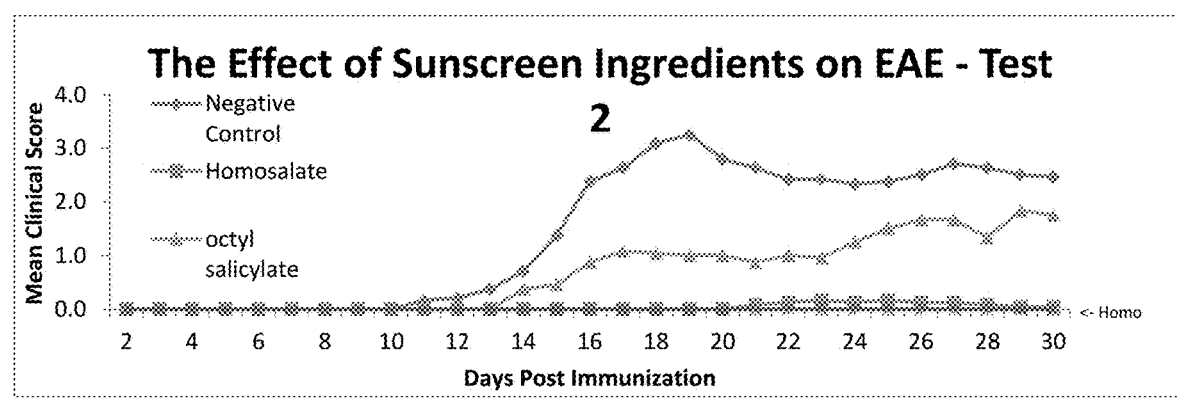
FIGS. 3A and 3B are a set of graphs showing the effect of sunscreen ingredients on EAE.
Figure 3B:
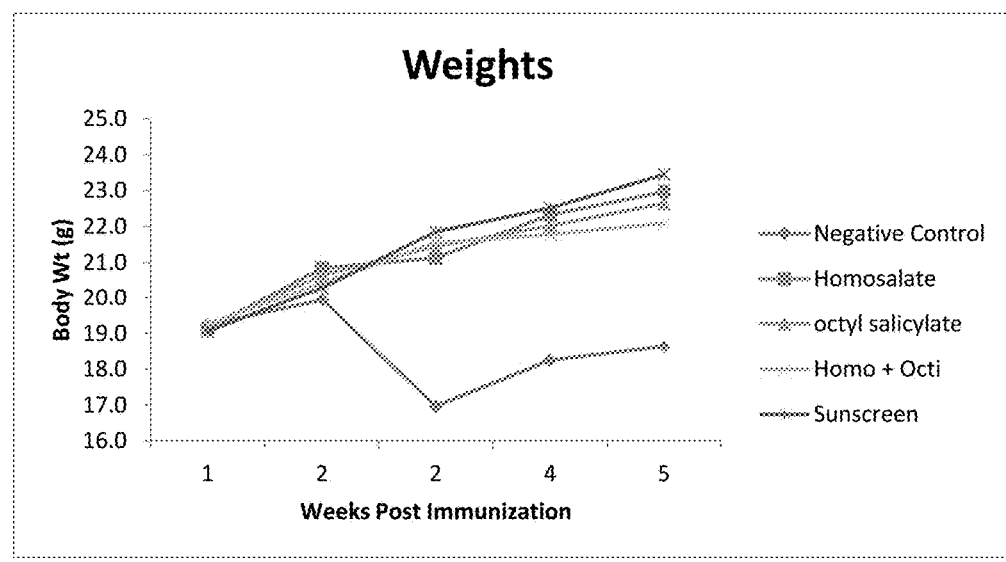

Referring to FIGS. 3A and 3B, sunscreen ingredients (homosalate and octyl salicylate) dramatically suppress EAE development in mice without affecting body weight. Mice were treated with ingredients (homosalate, octyl salicylate or combination) of sunscreen by topical administration daily during EAE (day 0-day 30). Sunscreen spray 200 µl daily was used as a positive control. Mice were scored daily and weighed weekly. Data were expressed as mean value, N=10-12/group.

Table 1, below, summarized the effect of different sunscreen ingredients on EAE mice.

TABLE 1

| Treatment | Incidence | Day of onset | Mean Severity | CDI |
|---|---|---|---|---|
| Control | 100% (12/12) | 16 ± 1 | 2.5 ± 0.8 | 42 ± 1 |
| Homosalate | 8% (1/12) * | 22 ± 0 * | 1.3 ± 0.0 * | 1 ± 0 * |
| octyl salicylate | 75% (9/12) | 18 ± 3 * | 2.0 ± 0.8 * | 20 ± 1 * |
| Homo + Octi | 0% (0/12) * | 0 ± 0 * | 0.0 ± 0.0 * | 0 ± 0 * |
| Sunscreen | 0% (0/11) * | 0 ± 0 * | 0.0 ± 0.0 * | 0 ± 0 * |

Data were expressed as mean ± SD.
N = 11-12;
* $P < 0.05$ vs Control.

Example 2

Salate Derivatives Found in Sunscreens Block Experimental Autoimmune Encephalomyelitis in Mice.

Abstract

Ultraviolet light (UV) suppresses experimental autoimmune encephalomyelitis (EAE, an animal model of MS) in mice and may be responsible for decreased incidence of MS in equatorial regions.

To test this concept further, we applied commercially available sunblock preparations to mice before exposure to UV light. Surprisingly, some of the sunblock preparations blocked EAE without UV light. Further, various sunblock preparations had variable ability to suppress EAE. By examining the components of the most effective agents, we found that homosalate and octisalate were the components responsible for suppressing EAE. Salates therefore maybe useful in stopping the progression of MS and may provide new insight into mechanisms of controlling autoimmune disease.

Significance

Multiple sclerosis (MS) is an autoimmune disease that is difficult to manage and for which there is no cure. We have discovered that certain specific sunblock preparations can prevent the development of experimental autoimmune encephalomyelitis (EAE), a widely used animal model of MS. Salate esters in the sunblock preparations were found responsible for preventing EAE. This suggests that the salate esters may be of value in arresting the symptoms of MS.

Introduction

Multiple sclerosis (MS) is a chronic inflammatory autoimmune disease of the central nervous system (CNS), affecting 2.5 million people worldwide (1). In 1974, Agranoff and Goldberg observed that the incidence of MS is inversely related to the sun exposure in both hemispheres (2). Goldberg suggested that increased vitamin D production caused by sunlight exposure may be responsible for the reduction of MS incidence (3). However, more recent results have made this hypothesis unlikely and instead a narrow band of UVB (NBUVB) light at 300-315 nanometers has been shown to suppress experimental autoimmune encephalomyelitis (EAE), the animal model of MS (4). This narrow band of light does not cause synthesis of Vitamin D from 7-Dehydrocholesterol (5). During the course of our studies we used commercial sunblock preparations presumably to prevent the suppression of EAE by NBUVB. Quite unexpectedly some sunblock preparations themselves completely prevented EAE without UV light. Further, commercial sunblock preparations varied widely in their ability to suppress EAE. By examining the components of the preparations, we found that two components were responsible for suppression of EAE. These two components are esters of salicylic acid i.e. homosalate and octisalate. We now report these findings.

Results

Topical Application of Sunscreen (Coppertone Spray) Completely Suppressed EAE Development.

Figure 4A:
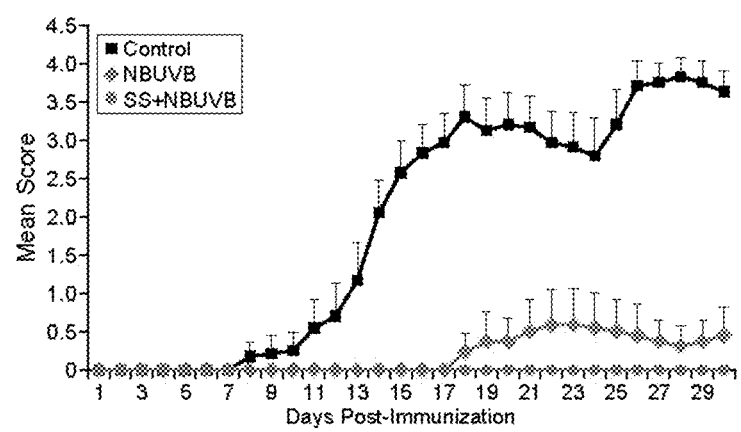
FIGS. 4A, 4B, and 4C show that topical application of COPPERTONE SPRAY sunscreen (SS) completely blocks EAE.
Figure 4B:
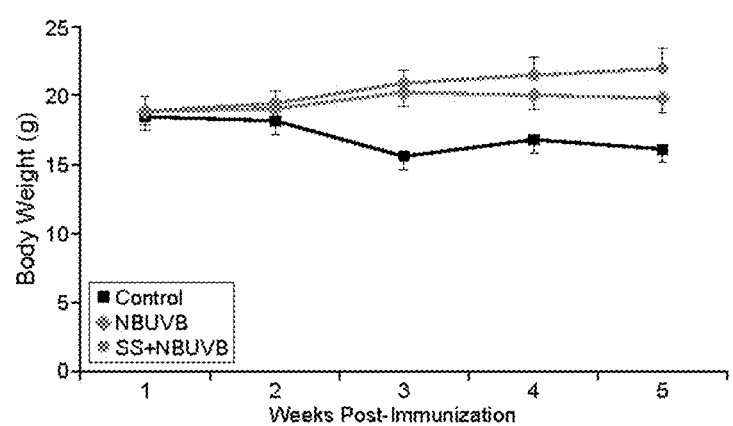
Figure 4C:
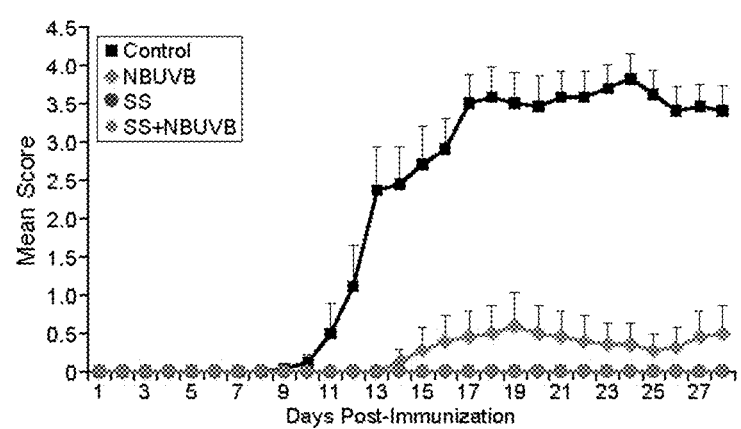

When mice were treated with NBUVB, the average disease severity was dramatically decreased similar to previous studies (FIG. 4A). Sunscreen application prior to NBUVB did not prevent the suppression by NBUVB (FIGS. 4A and 4C). The body weight changes observed in these animals was consistent in the disease outcome (FIG. 4B). Surprisingly, topical administration of sunscreen itself completely blocked EAE (FIG. 4C).

Commercial Sunscreens Differ Markedly in their Ability to Suppress EAE.

Figure 5A:
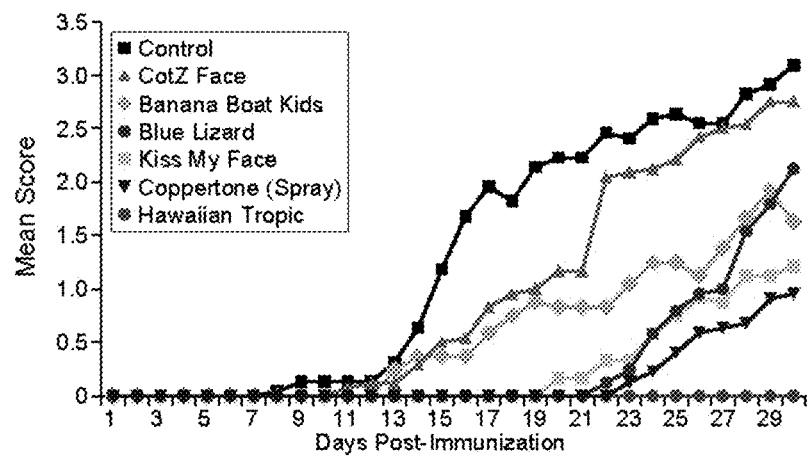
FIGS. 5A and 5B show that commercial sunscreen preparations differentially block EAE while darkness itself does not.
Figure 5B:
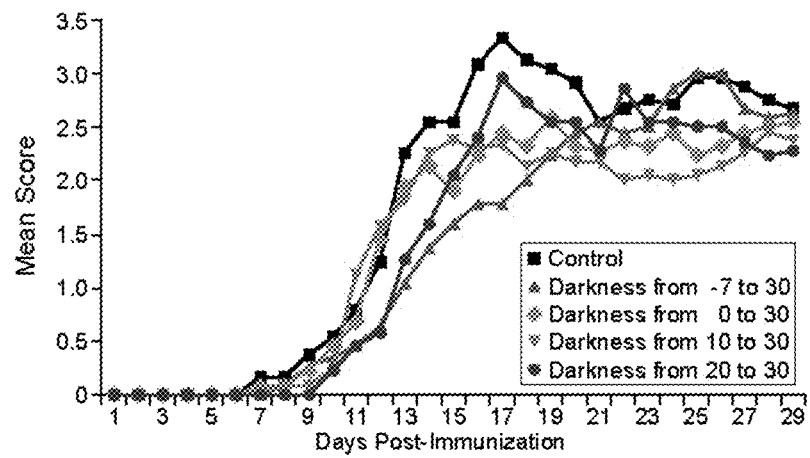
Figure 6A:
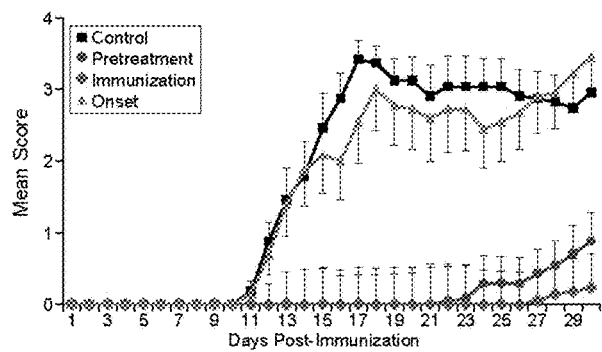
FIGS. 6A, 6B, 6C and 6D show that the suppression of EAE by COPPERTONE SPRAY sunscreen (SS) is both time and dose dependent.
Figure 6B:
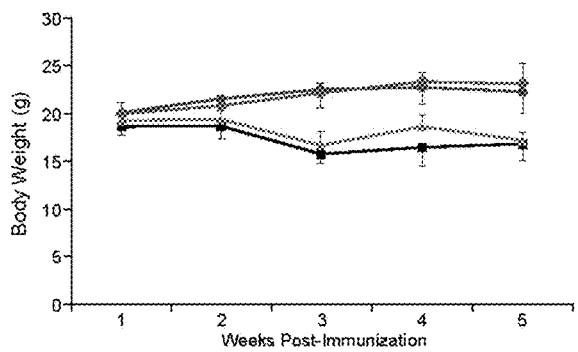
Figure 6C:
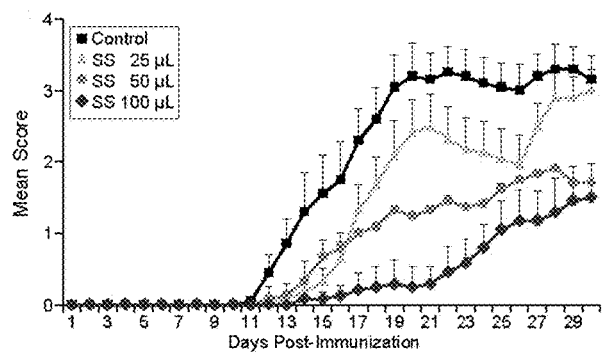
Figure 6D:
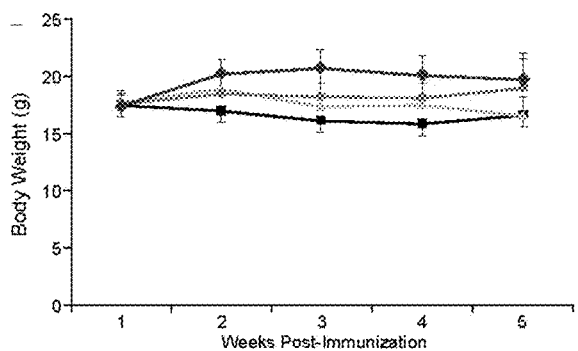

When 6 brands of sunscreen were tested on EAE, only 4 brands (HAWAIIAN TROPIC, COPPERTONE, KISS MY FACE, BLUE LIZARD) produced a significant suppression (FIG. 5A), the remaining two brands of sunscreen (BANANA BOAT, COTZ FACE) were without effect (FIG. 5A). To be sure that the effect of the sunscreen simply did not prevent a total block of all wavelengths, total darkness (−7 to 30 days) was tested and was without effect on EAE regardless of when it was initiated (FIG. 5B). Interestingly, additional testing indicated that sunscreen application was necessary at the time of immunization (FIG. 6A). The body weights were slightly but significantly higher in mice receiving treatment with sunscreen either prior to or at the time of immunization (FIG. 6B). The suppression of disease by sunscreen was dose-dependent (FIG. 6C) and increased body weights correlated with the improvement of disease (FIG. 6D).

Homosalate and Octisalate were the Ingredients that Caused EAE Suppression; Avobenzone and Oxybenzone Produced Only Slight Suppression of EAE.

Figure 7A:
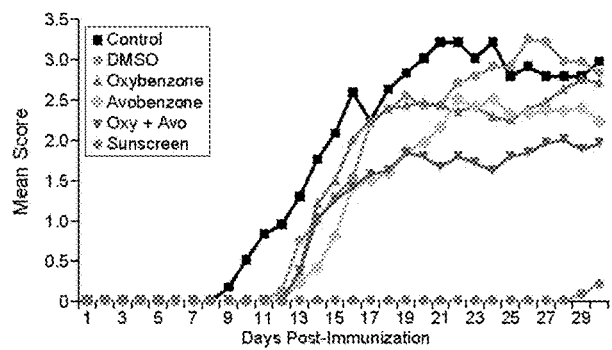
FIGS. 7A, 7B, 7C and 7D show that two ingredients of effective sunscreen (Homosalate and octisalate) significantly suppress EAE. Two other ingredients (avobenzone and oxybenzone) fail to suppress EAE.
Figure 7B:
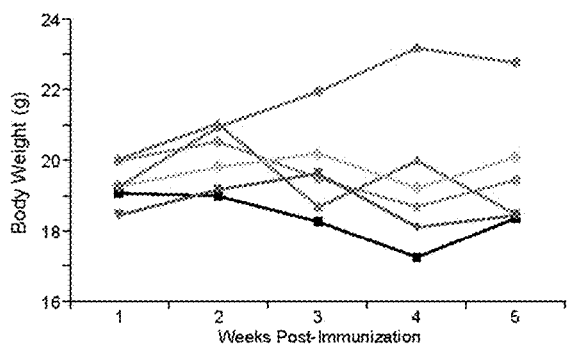
Figure 7C:
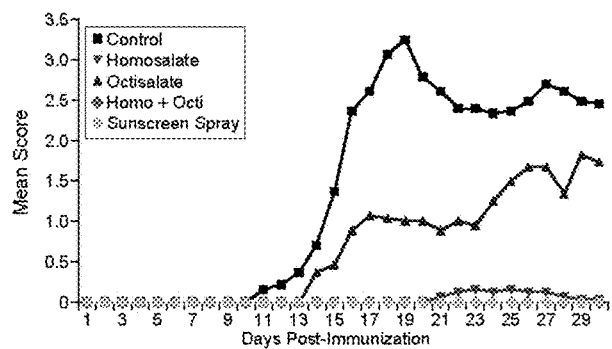
Figure 7D:
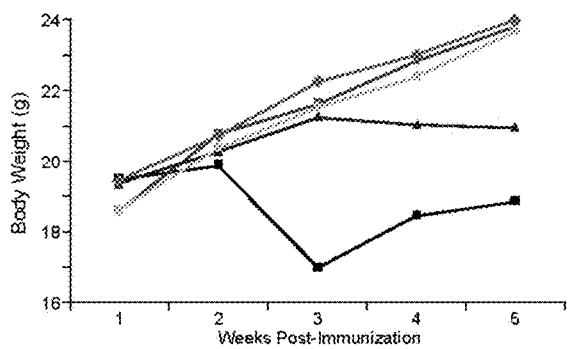

A dose of 30 μl homosalate (1.5 g/kg) and 10 μl octisalate (0.5 g/kg) were calculated to be the amount delivered by Coppertone Spray sunscreen. This quantity was applied to the mice. Sunscreen spray at 200 μl (containing homosalate 15%, octisalate 5%) was applied to EAE mice as a positive control. The results showed that homosalate only and a combination of homosalate and octisalate dramatically suppressed EAE severity. (FIG. 7C and Table 1). Octisalate at the dose of 0.5 g/kg produced a moderate suppression but did not reach statistical significance (FIG. 7C and Table 1). The degree of the disease was reflected in body weight (FIG. 7D). The other two ingredients (avobenzone and oxybenzone) and the combination produced little to no significant suppression of EAE (FIG. 7A) and no significant change in body weight (FIG. 7B).

Homosalate and Octisalate Suppression was Dose Dependent.

When tested at three different doses (0.5, 1.0, 1.5 g/kg), both homosalate and octisalate exhibited dose-dependent suppression of EAE (FIG. 8A). With the exception of the lowest dose of homosalate, all treatments increased the body weight (FIG. 8B). When homosalate was applied less frequently than each day, its effectiveness diminished (FIGS. 8C and 8D).

Discussion

Because UV light and especially narrow band UV light can suppress EAE, it was surprising to find that sunblock creams could prevent the development of EAE even in the absence of UV light. On closer examination it became clear that not all sun block preparations possess this property. Further, complete absence of light was without effect on EAE. We thus focused on the component(s) of the active sunblock preparations. The suppression of EAE by the active sunblock preparations was traced to two salate esters i.e. homosalate and octasalate. When tested directly both salates were equally active at ca 1.5 g/kg in suppressing EAE. It is likely that these compounds are not acting by blocking or absorbing UV light. Simply keeping mice in a complete absence of light did not affect the development of EAE. Further, some sunscreens that are effective as sun blockers do not suppress EAE. Only sunblocks that contain salate esters are effective and the salates themselves clearly block EAE. The only adverse effect of the homosalate and octisalate is a temporary mild skin irritation. A topical dose of 1.5 g/kg of homosalate, which completely blocked EAE, is below the unpublished acute dermal toxicity (LD50>5 g/kg for rabbits).

The complete suppression of EAE by topical administration of homosalate and octisalate is a novel finding. Salicylates are well-known nonsteroidal anti-inflammatory drugs (NSAIDs)(6). The anti-inflammatory effect of homosalate has been demonstrated in another study by using the ear edema test in mice (7). A related compound, aspirin (acetylsalicylic acid, ASA) is a traditional anti-inflammatory pharmaceutical (8). The relationship between aspirin and MS was studied in 1961 without a significant difference between the control and treated group (9). There has not been a direct study of aspirin and MS development. Inhibition of cyclooxygenase (COX) is the primary mechanism of NSAID (10). COX-2 has been observed in MS lesions (11). Recently, cyclooxygenase (COX) inhibitors, have shown significant suppression of EAE (12, 13). It is clear that we have no explanation of how the salates prevent EAE. However, this finding presents a clear opportunity to explore not only mechanisms but also new approaches to therapy of MS.

Materials and Methods

Animal Husbandry.

Female C57BL/6 mice (8-10 weeks old) purchased from Jackson Laboratory (Bar Harbor, Me.) were fed a standard lab chow 5008 (Purina Mills, Richmond, Ind.). The mice were exposed to 12 h light-dark cycles. In one experiment the animals were kept in darkness at all times. All procedures were approved by the Institutional Animal Care and Use Committee of the College of Agricultural & Life Sciences, University of Wisconsin-Madison.

EAE Induction

Mice were immunized with $MOG_{35-55}$ kit (EK-2110, purchased from Hooke lab (Lawrence, Mass.)). Each mouse was immunized with a subcutaneous injection of 20 μl $MOG_{35-55}$/CFA emulsion and an intraperitoneal injection with 200 ng of pertussis toxin (List Biological Laboratories) diluted in sterile PBS (14). A second booster pertussis toxin injection was given 48 hours later. Each mouse was scored daily for clinical signs of EAE using the following scale: 0, no clinical disease; 1, loss of tail tone; 2, unsteady gait; 3, hindlimb paralysis; 4, forelimb paralysis; 5, death (15).

Sunscreens and Active Ingredients Treatment

Sunscreen creams or spray applied topically to the shaved back skin of the mice daily are shown below (Table 2): 1. BANANA BOAT KIDS(SPF 50, Energizer Personal Care, LLC, Shelton, Conn.); 2. BLUE LIZARD AUSTRALIAN SUNSCREEN (SPF 30, Crown Laboratories, Johnson, Tenn.) 3. COPPERTONE SPRAY (SPF 50, MSD Consumer Care, Inc., Memphis, Tenn.); 4. COTZ FACE (SPF40, CoTZ Skincare, West Norriton, Pa.); 5. HAWAIIAN TROPIC (SPF 50, Energizer Personal Care, LLC, Shelton, Conn.); 6. KISS MY FACE (SPF 50, Kiss My Face, LLC, Gardiner, N.Y.). Each sunscreen was applied daily to cover the shaved skin (100-200 μl). Avobenzone, oxibenzone, homosalate, and octisalate were purchased from Spectrum Chemical Mfg. Corp. (New Brunswick, N.J.). Avobenzone and oxibenzone were dissolved in DMSO. Homosalate and octisalate were applied directly. The total dose of each ingredient administrated topically on each mouse skin was equal to the amount provided by the respective sunscreen.

TABLE 2

Sunscreen brands tested.

| Trade name | SPF | Active Ingredients |
|---|---|---|
| Banana Boat Kids | 50 | Titanium dioxide 3.1%, Zinc oxide 4.0% |
| Blue Lizard | 30 | Octinoxate 7.5%, Octicrylen 2.0%, Oxybenzone 3.0%, Zinc oxide 6.0% |
| Coppertone (Spray) | 50 | Avobenzone 3.0%, Homosalate 15.0%, Octisalate 5.0% |
| CoTZ Face | 40 | Titanium dioxide 8.0%, Zinc oxide 3.8% |
| Hawaiian Tropic | 50 | Avobenzone 2.7%, Homosalate 8.0%, Octisalate 4.5%, Octocrylen 5.0% |
| Kiss My Face | 50 | Avobenzone 4.0%, Homosalate 5.0%, Octinoxate 7.5%, Octisalate 5.0%, Zinc oxide 1.7% |

Narrow Band UVB (NBUVB) Treatment

For NBUVB treatment, a set of four TL20W/01 UVB 311 narrow band 2 ft. bulbs (wavelength centered at 311-313 nm, Amjo Corp, West Chester, Ohio) were used daily at (10 $KJ/m^2$) (14). The radiation output was measured using a UV radiometer equipped with a 302-nm sensor (UVP LLC, Upland, Calif.). A 16-chamber Plexiglass cage was used for daily UV radiation. Each chamber contained one mouse. The mice were rotated through the different chambers so that each mouse received equal light exposure. The mice were UV radiated beginning at the same day of immunization continuing through 30 days post immunization.

REFERENCES

1. Compston A & Coles A (2002) Multiple sclerosis. *Lancet* (London, England) 359(9313):1221-1231.
2. Agranoff B W & Goldberg D (1974) Diet and the geographical distribution of multiple sclerosis. *Lancet* (London, England) 2(7888):1061-1066.
3. Goldberg P (1974) Multiple sclerosis: vitamin D and calcium as environmental determinants of prevalence. *International Journal of Environmental Studies* 6(1):19-27.
4. Wang Y, et al. (2013) Suppression of experimental autoimmune encephalomyelitis by 300-315 nm ultraviolet light. *Archives of biochemistry and biophysics* 536(1):81-86.
5. MacLaughlin J A, Anderson R R, & Holick M F (1982) Spectral character of sunlight modulates photosynthesis of previtamin D3 and its photoisomers in human skin. *Science* (New York, N.Y.) 216(4549):1001-1003.
6. Paulus H E & Whitehouse M W (1973) Nonsteroid anti-inflammatory agents. *Annual review of pharmacology* 13:107-125.
7. Couteau C, Chauvet C, Paparis E, & Coiffard L (2012) UV filters, ingredients with a recognized anti-inflammatory effect. *PloS one* 7(12):e46187.
8. Tsau S, Emerson M R, Lynch S G, & LeVine S M (2015) Aspirin and multiple sclerosis. *BMC medicine* 13:153.
9. Miller H, Newell D J, & Ridley A (1961) Multiple sclerosis. Trials of maintenance treatment with prednisolone and soluble aspirin. *Lancet* (London, England) 1(7169): 127-129.
10. Farah A E & Rosenberg F (1980) Potential therapeutic applications of aspirin and other cyclo-oxygenase inhibitors. *British journal of clinical pharmacology* 10 Suppl 2:261s-278s.

11. Rose J W, Hill K E, Watt H E, & Carlson N G (2004) Inflammatory cell expression of cyclooxygenase-2 in the multiple sclerosis lesion. *Journal of neuroimmunology* 149(1-2):40-49.
12. Miyamoto K, et al. (2006) Selective COX-2 inhibitor celecoxib prevents experimental autoimmune encephalomyelitis through COX-2-independent pathway. *Brain: a journal of neurology* 129(Pt 8):1984-1992.
13. Marusic S, et al. (2008) Blockade of cytosolic phospholipase A2 alpha prevents experimental autoimmune encephalomyelitis and diminishes development of Th1 and Th17 responses. *Journal of neuroimmunology* 204(1-2):29-37.
14. Wang Y, Marling S J, Martino V M, Prahl J M, & Deluca H F (2016) The absence of 25-hydroxyvitamin D3-1alpha-hydroxylase potentiates the suppression of EAE in mice by ultraviolet light. *The Journal of steroid biochemistry and molecular biology*.
15. Becklund B R, Severson K S, Vang S V, & DeLuca H F (2010) UV radiation suppresses experimental autoimmune encephalomyelitis independent of vitamin D production. *Proceedings of the National Academy of Sciences of the United States of America* 107(14):6418-6423.

The invention claimed is:

1. A method of treating a prospective multiple sclerosis (MS) patient, comprising the steps of:
   (a) Identifying a prospective MS patient, and
   (b) Treating the patient with an effective amount of a composition selected from the group consisting of homosalate, octyl salicylate and combinations of homosalate and octyl salicylate, wherein occurrence of MS symptom is lessened or progression of the symptom is slowed or stalled.
2. The method of claim 1, wherein the symptom is muscle weakness/numbness.
3. The method of claim 1, wherein the treatment is daily.
4. The method of claim 1, wherein the treatment is at least 30 days in duration.
5. The method of claim 1, wherein the composition is delivered as an oral dose.
6. The method of claim 1, wherein the composition is delivered as a topical dose.
7. The method of claim 1, wherein the composition is delivered as a parenteral dose.
8. The method of claim 1, wherein the composition comprises homosalate or the combination of homosalate and octyl salicylate.
9. The method of claim 1, wherein the compositions consist essentially of homosalate.
10. The method of claim 1, wherein the composition consists essentially of the combination of homosalate and octyl salicylate.

* * * * *

UNITED STATES PATENT AND TRADEMARK OFFICE
CERTIFICATE OF CORRECTION

PATENT NO. : 11,266,664 B2
APPLICATION NO. : 16/549677
DATED : March 8, 2022
INVENTOR(S) : Hector F. DeLuca et al.

Page 1 of 1

It is certified that error appears in the above-identified patent and that said Letters Patent is hereby corrected as shown below:

In the Specification

Column 2, Line 12, "N=1-12/group" should be --N=11-12/group--.

Signed and Sealed this
Twentieth Day of August, 2024

Katherine Kelly Vidal
Director of the United States Patent and Trademark Office